United States Patent [19]

Chibata et al.

[11] 4,124,636

[45] Nov. 7, 1978

[54] METHOD OF PREPARING MONOPOTASSIUM L-MALATE AND ITS MONOHYDRATE

[75] Inventors: Ichiro Chibata, Suita; Akihiko Sumi, Ashiya; Osamu Ohtsuki, Nagaokakyo, all of Japan

[73] Assignee: Tanabe Seiyaku Co., Ltd., Osaka, Japan

[21] Appl. No.: 876,698

[22] Filed: Feb. 10, 1978

[30] Foreign Application Priority Data

Feb. 18, 1977 [JP] Japan .................................. 52-17511

[51] Int. Cl.² ............................................. C07C 59/22
[52] U.S. Cl. .................................................... 562/402
[58] Field of Search ..................................... 260/535 P

[56] References Cited

U.S. PATENT DOCUMENTS 3,435,070  3/1969  Cheng .............................. 260/535 P
4,057,577  11/1977  Suzuki ............................. 260/535 P

*Primary Examiner*—Paul J. Killos
*Attorney, Agent, or Firm*—Bierman & Bierman

[57] ABSTRACT

An aqueous solution of L-malic acid and potassium ion is prepared having a pH of no more than 6.8. The aqueous solution is cooled to initiate crystallization of a potassium salt of L-malic acid, and the aqueous mixture obtained is allowed to stand at a pH of 5.3 to 6.8 until it substantially reaches liquid-solid equilibrium. The resultant crystals of monopotassium L-malate monohydrate are collected therefrom. The monopotassium L-malate monohydrate thus obtained may be dried to give the corresponding anhydrate. Monopotassium L-malate and its monohydrate are stable, non-hygroscopic crystals.

23 Claims, 2 Drawing Figures

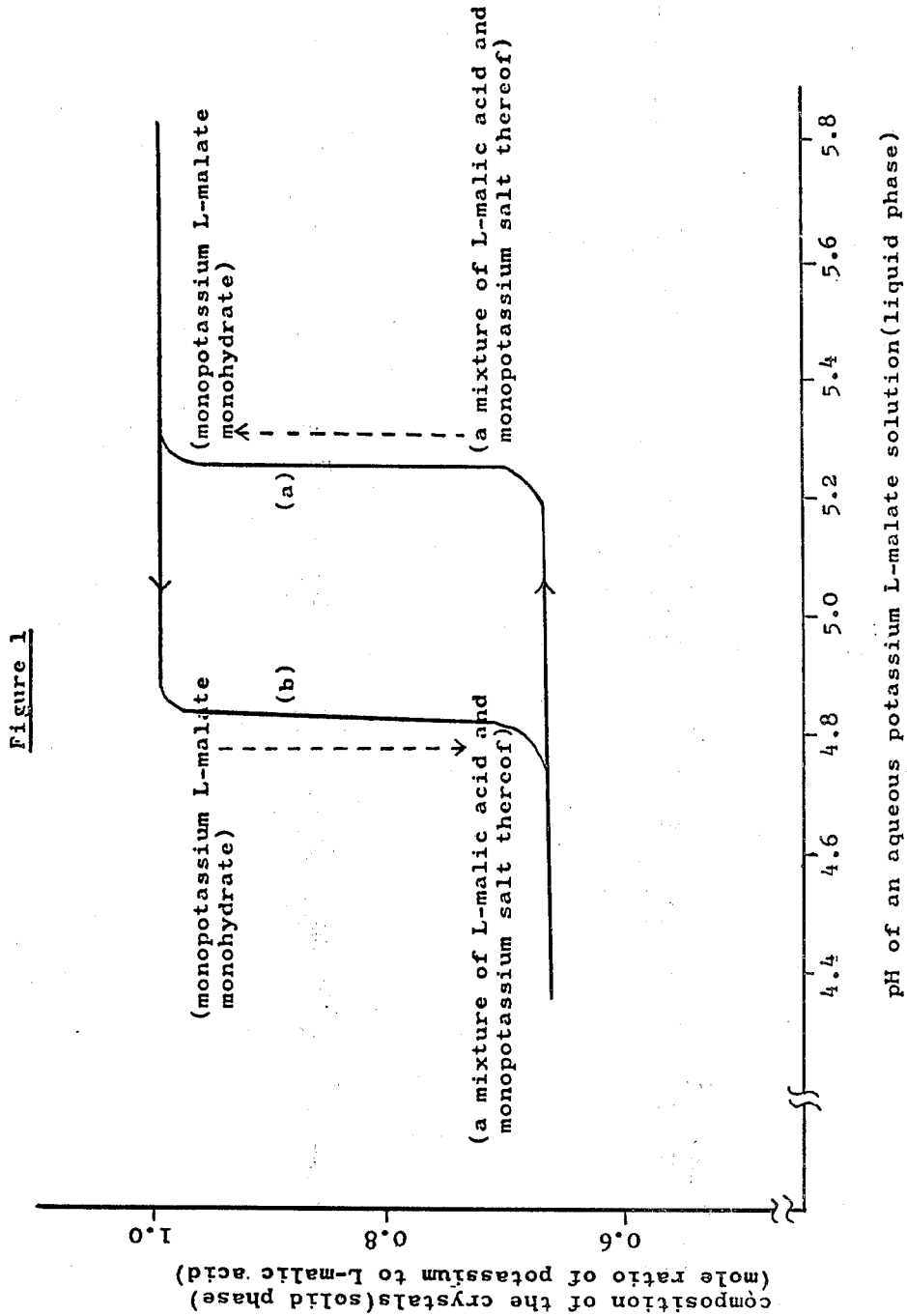

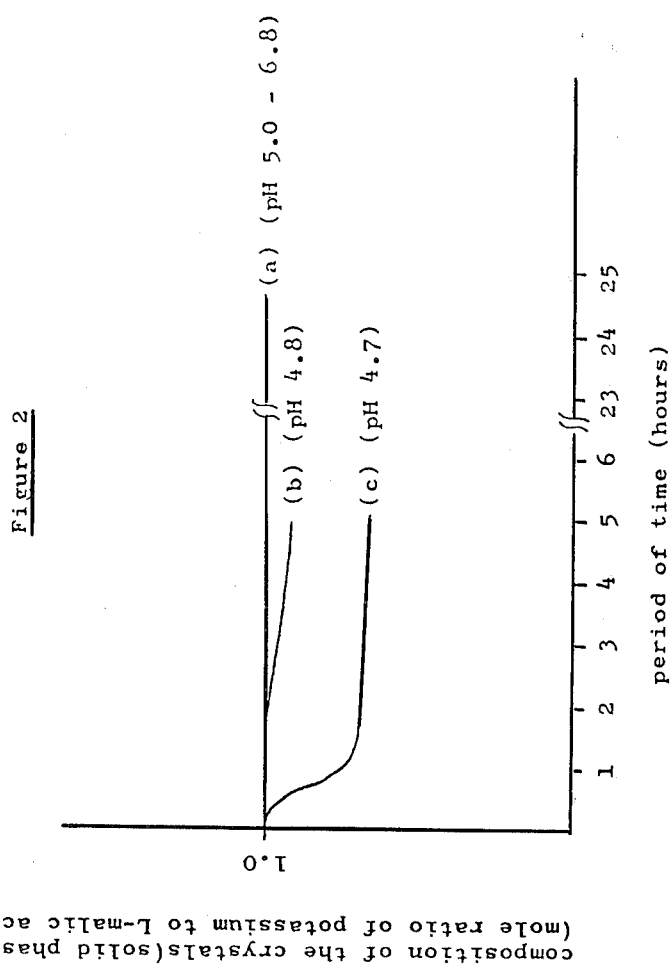

METHOD OF PREPARING MONOPOTASSIUM L-MALATE AND ITS MONOHYDRATE

BACKGROUND OF THE INVENTION

This invention relates to a method of preparing monopotassium L-malate and its monohydrate.

Potassium is an important cationic constituent in living bodies and a potassium salt of the L-malic acid is useful in the treatment of hypo-potassemia.

It is known in the art that the hygroscopic character of dipotassium DL-malate makes it difficult to prepare and store said salt in solid form. In order to improve the hygroscopicity of dipotassium DL-malate, attempts have been made to prepare the corresponding monohydrate. For example, U.S. Pat. No. 3,435,070 discloses that dipotassium DL-malate monohydrate is prepared by adjusting the pH of an aqueous DL-malic acid solution to between 7.0 and 9.0 with potassium carbonate, concentrating the solution at a temperature of at least 110° C., and then cooling the concentrated solution to below about 30° C. Alternatively, Japanese Patent Application No. 76,518/1975 (laid open to the public under No. 3,019/1977) discloses that dipotassium DL-malate monohydrate is prepared by reacting DL-malic acid with potassium hydroxide in an aqueous alcohol, adjusting the pH of the reaction solution to between 7 and 9.5, and then recovering the precipitates therefrom. However, dipotassium L-malate and its monohydrate are highly soluble in water and can not be obtained as crystals by these known methods even by employing L-malic acid instead of DL-malic acid as the starting material.

In addition to the above-mentioned methods, an aqueous solution of monopotassium L-malate may be obtained by mixing L-malic acid with an equimolar amount of potassium ion in water. However, monopotassium L-malate is different from the corresponding sodium salt and monopotassium DL-malate with respect to their crystallographic properties and it is impossible to recover the pure crystals of monopotassium L-malate from said aqueous solution by conventional methods. For example, the crystals which are recovered from said aqueous solution by refrigeration and/or concentration are composed of one mole of L-malic acid and between about 0.6 and 0.8 mole of potassium ion.

SUMMARY OF THE INVENTION

As a result of our investigations, we have now found that when L-malic acid and potassium ion are dissolved in an aqueous solvent at a pH higher than 6.8, a malic acid salt contained in the solution exists substantially in the form of dipotassium L-malate and can not be crystallized out from the aqueous solvent. In this connection, however, we have also found that crystals of monopotassium L-malate monohydrate or crystals composed of L-malic acid and monopotassium L-malate are obtained by cooling an aqueous solution of L-malic acid and potassium ion at a pH of 6.8 or less. Namely, pure crystals of monopotassium L-malate monohydrate are obtained by cooling an aqueous solution of L-malic acid and potassium ion having a pH of 6.8 or less, to initiate crystallization of a potassium salt of L-malic acid, and continuing said crystallization at a pH of 5.3 to 6.8, especially at a pH of 5.3 to 6.5. On the other hand, when the crystallization step described above is continued at a pH lower than 5.3, the crystals obtained as the solid phase are composed of L-malic acid and monopotassium L-malate. Moreover, we have found that pure crystals of monopotassium L-malate monohydrate can also be prepared from impure crystals composed of L-malic acid and monopotassium L-malate by allowing said impure crystals to stand in a small amount of water at a pH of 5.3 to 6.8 until liquid-solid equilibrium is substantially achieved.

An object of the present invention is to provide a practical and economical method for preparing monopotassium L-malate monohydrate and its anhydrate in stable, non-hygroscopic forms. Another object of the invention is to provide a method of preparing highly pure monopotassium L-malate monohydrate and its anhydrate in a high yield. Other objects of the present invention will be clearly observed from the description which follows.

Throughout the specification and claims, the term "potassium L-malate" should be interpreted as another designation for "a potassium salt of L-malic acid" including monopotassium L-malate, dipotassium L-malate, a mixture of mono- and di-potassium L-malate and even a mixture of at least one of these malates and free L-malic acid.

BRIEF EXPLANATION OF THE DRAWINGS

FIG. 1 shows the liquid-solid equilibrium relationship of potassium L-malate, i.e., the effect of the pH of an aqueous potassium L-malate solution (liquid phase) upon the composition of crystals of potassium L-malate (solid phase) in a two-phase system consisting of said liquid-solid phases. Line (a) in FIG. 1 was estimated by dissolving L-malic acid and potassium carbonate in water at about 60° C., cooling said solution to crystallize out the malic acid salt, and then allowing the resultant aqueous mixture (i.e., the mixture of crystals precipitated and the aqueous potassium L-malate solution) to stand at 10° C. and at a pH specified therein. The pH of said aqueous mixture was adjusted with potassium carbonate. The composition of the crystals was analyzed after said aqueous mixture substantially reached liquid-solid equilibrium. On the other hand, line (b) in FIG. 1 shows the stability of crystals of monopotassium L-malate monohydrate. The stability of the L-malic acid salt was estimated in terms of the changes in composition of the crystals and was examined by suspending crystals of monopotassium L-malate monohydrate in an aqueous potassium L-malate solution at 10° C. and at a pH specified therein for 24 hours.

FIG. 2 also shows the stability of crystals of monopotassium L-malate monohydrate, i.e., the changes in composition of said crystals with the passage of time. The stability at 10° C. of the L-malic acid salt estimated at a pH of 5.0–6.8, 4.8 and 4.7 is shown as lines (a), (b) and (c), respectively.

DESCRIPTION OF THE INVENTION INCLUDING PREFERRED EMBODIMENTS

According to the present invention, monopotassium L-malate monohydrate can be prepared by cooling an aqueous solution of L-malic acid and potassium ion, having a pH of 6.8 or less, to initiate crystallization of potassium L-malate, continuing said crystallization at a pH of 5.3 to 6.8, and recovering the crystals of monopotassium L-malate monohydrate therefrom.

An aqueous solution of L-malic acid and potassium ion, having a pH of 6.8 or less, can be prepared in a conventional manner. For example, said aqueous solution can be prepared by dissolving L-malic acid in an aqueous solvent and adding a water-soluble potassium salt thereto. Potassium carbonate, potassium bicarbonate and potassium hydroxide are suitable as the water-soluble potassium salt. A suitable amount of the potassium ion which is added to the aqueous L-malic acid solution is between about one and 1.9 moles, especially between about 1.1 and 1.5 moles per mole of L-malic acid used. Examples of the aqueous solvent include water, aqueous methanol, aqueous ethanol, aqueous acetone and aqueous ethyl acetate. From an industrial point of view, water is most preferable as the aqueous solvent. The aqueous solution of L-malic acid and potassium ion may be prepared at any temperature between about 30° and 80° C., but it is especially preferred to make it between about 30° and 60° C. Further, the aqueous solution of L-malic acid and potassium ion may be prepared by adding an organic or inorganic acid to an aqueous dipotassium L-malate solution thereby adjusting its pH to 6.8 or less. L-malic acid per se is preferably employed to adjust the pH of the aqueous dipotassium L-malate solution, but hydrochloric acid, acetic acid and the like may also be employed for this purpose. The aqueous solution of L-malic acid and potassium ion obtained above may be, if required, condensed prior to the subsequent cooling step.

Then, the aqueous solution of L-malic acid and potassium ion, having a pH of 6.8 or less, is cooled to initiate crystallization of potassium L-malate, and this crystallization step is continued until a sufficient amount of crystals is obtained. It is preferable to cool said solution to a temperature below 50° C., especially to a temperature of between about 5° and 30° C. The crystallization step of the present invention should be continued at a pH of 5.3 to 6.8, especially at a pH of 5.3 to 6.5. As shown in FIG. 1-(a), the crystals of potassium L-malate exists only in the form of monopotassium L-malate monohydrate within the limited pH range of 5.3 to 6.8 by allowing the aqueous mixture (i.e., the mixture of said aqueous potassium L-malate solution and crystals precipitated) to stand at the pH specified above. While the above-mentioned aqueous mixture may be allowed to stand without stirring, the time required to complete crystallization can be shortened by allowing the aqueous mixture to stand under stirring. Moreover, it is preferable to continue this crystallization step until the aqueous mixture substantially reaches liquid-solid equilibrium, i.e., until it substantially reaches a static state with respect to spontaneous crystallization and dissolution of the L-malic acid salt. According to a preferred embodiment of the present invention, therefore, the two steps mentioned above (i.e., the cooling and subsequent crystallization steps) may be carried out by cooling an aqueous solution of L-malic acid and potassium ion, having a pH of 6.8 or less, to initiate crystallization of potassium L-malate, and allowing the resultant aqueous mixture (i.e., the mixture of said aqueous potassium L-malate solution and crystals precipitated) to stand at a pH of 5.3 to 6.8, especially at a pH of 5.3 to 6.5, until it substantially reaches liquid-solid equilibrium.

Crystals composed of L-malic acid and monopotassium L-malate may be obtained by cooling an aqueous solution of L-malic acid and potassium ion at a pH lower than 5.3; or by allowing the mixture of crystals precipitated and the aqueous potassium L-malate solution to stand at a pH lower than 5.3. Moreover, an aqueous solution containing an equimolar amount of L-malic acid and potassium ion usually has a pH of about 4.1, and crystals of the L-malic acid salt recovered therefrom are composed of L-malic acid and monopotassium L-malate. In these cases, the aqueous potassium L-malate solution or the mixture of said solution and crystals precipitated must be adjusted to a pH of 5.3 to 6.8, especially to a pH of 5.3 to 6.5, with an alkali reagent prior to the subsequent recovery of the crystals. Preferred examples of the alkali reagent which are employed for this purpose include potassium carbonate, potassium bicarbonate and potassium hydroxide. Instead of these potassium salts, however, sodium hydroxide, ammonia and the like may also be employed for the same purpose.

Recovery of the crystals of monopotassium L-malate monohydrate can be accomplished in a conventional manner. For example, it can be carried out by filtering or centrifuging the aqueous mixture obtained above [i.e., the mixture of the crystals of pure monopotassium L-malate monohydrate (solid phase) and the aqueous potassium L-malate solution (liquid phase)]. This procedure may be accomplished at a pH of 5.3 to 6.8, i.e., without changing the pH of the aqueous mixture. As shown in FIGS. 1 and 2, however, the crystals of monopotassium L-malate monohydrate once obtained remain stable even at a pH lower than 5.3 provided that the pH of the liquid phase is kept at a pH of at least 4.8 and the crystals are recovered promptly (e.g., within a period as short as 1 hour). On the other hand, the crystals of monopotassium L-malate monohydrate change swiftly to crystals composed of L-malic acid and monopotassium L-malate at a pH lower than 4.8. Accordingly, once monopotassium L-malate monohydrate is crystallized out as described hereinbefore, the recovery of the crystals can be carried out at a pH of 4.8 to 6.8. For example, the aqueous mixture composed of the aqueous potassium L-malate solution and the crystals of monopotassium L-malate monohydrate is adjusted to a pH of 4.8 with an acid (e.g., L-malic acid, hydrochloric acid, sulfuric acid), stirred for a short period of time such as 10 to 50 minutes and then filtered. Pure crystals of monopotassium L-malate monohydrate can be thereby recovered.

FIG. 1-(a) shows that, in the two-phase system consisting of crystals of potassium L-malate (solid phase) and an aqueous potassium L-malate solution (liquid phase), the crystals of said L-malate exist only in the form of monopotassium L-malate monohydrate if said liquid phase is kept at a pH of 5.3 to 6.8. FIG. 1-(a) also shows that, when the liquid phase of said two-phase system is kept at a pH lower than 5.3, the crystals (i.e., the solid phase) in said two-phase system are always composed of L-malic acid and monopotassium L-malate. Moreover, FIG. 1-(a) shows that the crystals (i.e., the solid phase) composed of L-malic acid and monopotassium L-malate change to pure crystals of monopotassium L-malate monohydrate with an increase in the pH of the liquid phase, i.e., by adjusting the liquid phase to a pH of 5.3 to 6.8. Therefore, impure crystals of monopotassium L-malate (e.g., crystals composed of L-malic acid and monopotassium L-malate, crystals composed of L-malic acid and dipotassium L-malate, or crystals composed of monopotassium L-malate and dipotassium L-malate) can be readily purified by taking advantage of these properties of potassium L-malate. Namely, according to the present invention, pure crystals of monopotassium L-malate monohydrate can be prepared from impure crystals (i.e., crystals composed of at least two components selected from L-malic acid, monopotassium L-malate and dipotassium L-malate) by the steps of (i) adding the latter crystals to sufficient water to produce a mixture of the crystals added and an aqueous potassium L-malate solution; (ii) adjusting the aqueous mixture to a pH of 5.3 to 6.8, especially to a pH of 5.3 to 6.5; (iii) allowing the aqueous mixture to stand at the same pH range until it substantially reaches liquid-solid equilibrium; and then (iv) recovering the resultant crystals therefrom. The crystals composed of L-malic acid and monopotassium L-malate may be usually obtained by cooling an aqueous potassium L-malate solution at a pH lower than 5.3; or by adding the excess amount of crystals of L-malic acid to the aqueous solution of a water-soluble potassium salt, followed by agitation thereof at a pH lower than 5.3. Water-soluble potassium salts such as potassium carbonate, potassium bicarbonate, potassium hydroxide and the like are preferably employed to adjust the pH of the aqueous mixture (i.e., the mixture of the crystals added and the aqueous potassium L-malate solution). In allowing the aqueous mixture to stand at the pH specified above, it is preferred to carry it out under stirring. The crystals thus obtained can be recovered in a conventional manner, for example, by filtration or centrifugation. As described hereinbefore, the recovery of the crystals may be carried out at a pH of 4.8 to 6.8.

Monopotassium L-malate monohydrate obtained above can be readily converted to crystals of monopotassium L-malate anhydrate by drying the former salt in hot air of low humidity. For example, the crystals of monopotassium L-malate anhydrate are prepared preferably by drying the corresponding monohydrate in hot air at 50° C. under a relative humidity lower than 31%.

It is seen from the aforementioned description that the method of the present invention can be carried out simply and conveniently. For example, the condensed aqueous dipotassium DL-malate solution of U.S. Pat. No. 3,435,070 becomes a viscous syrup or a heavy slurry and crystallization of said dipotassium salt can not frequently be completed within 16 hours to a few days. On the other hand, the method of the present invention can be completed within a shorter period such as a few to several hours. In addition, in carrying out the method of Japanese Patent Application No. 76,518/1975, excess alcohol must be employed as the solvent because otherwise dipotassium DL-malate monohydrate is obtained as viscous oil and it becomes difficult to separate the malic acid salt by filtration. Unlike that of said Japanese Patent Application, however, the method of the present invention makes it possible to prepare crystalline, non-hygroscopic, fine precipitates of monopotassium L-malate monohydrate without using excess alcohol. Moreover, commercially available L-malic acid is usually contaminated with fumaric acid and other impurities. Further, since fumaric acid is much more soluble in water than L-malic acid, it is difficult to remove such impurities completely by conventional methods. The method of the present invention is advantageous in that such impurities as fumaric acid are removed preferably during the operation of the invention and highly pure crystals of monopotassium L-malate or its monohydrate are always obtained even by employing impure L-malic acid as the starting material thereof. Concomitantly, although an aqueous solution of L-malic acid or L-malate can not be condensed to dryness without decomposition of L-malic acid, the method of the present invention is also advantageous in that it can be carried out without such decomposition of L-malic acid.

Monopotassium L-malate monohydrate and its anhydrate obtained in the present invention are stable, non-hygroscopic crystals and are particularly suitable for medicinal use, as for example in the treatment of hypopotassemia.

Practical and presently-preferred embodiments of the present invention are illustratively shown in the following Examples. Throughout the Examples, the water content of the samples is assayed by the Karl-Fisher method[Pharmacopoeia Japonica, Editio Nona, pages 660 -662(1976)]. On the other hand, the L-malic acid content of the samples is assayed by treating an aqueous solution of said sample with a cation exchange resin and then titrating the effluent with 1N sodium hydroxide. The potassium content of the samples is assayed by treating an aqueous solution of said samples with an anion exchange resin and then titrating the effluent with 1 N hydrochloric acid.

EXAMPLE 1

(1) 134.1 g (one mole) of L-malic acid are dissolved in 400 ml of water, and 84.3 g (0.61 mole) of potassium carbonate are added to the L-malic acid solution under stirring. The solution (pH 4.4) is concentrated under reduced pressure at 60° C. to make the total volume thereof about 250 ml. The concentrated aqueous solution is gradually cooled to 10° C. Then, the mixture thus obtained (i.e., the mixture of the concentrated aqueous solution and crystals precipitated) is stirred at the same temperature for 2 hours. After stirring, the mixture had a pH of 5.5. The crystalline precipitates are collected by filtration, washed with an aqueous 80% methanol solution and dried at 35° C. in air for 24 hours. 136.6 g of monopotassium L-malate monohydrate are obtained as crystals. Yield: 71.8% The product loses its intramolecular water at 98° to 100° C. and decomposes at 184° to 185° C.

$[\alpha]_D^{22} - 5.6°$ (C=4, in water)

Analysis calculated for $KC_4H_5O_5 H_2O$:
C, 25.26; H, 3.72; K, 20.56
Found: C, 25.32; H, 3.78; K, 20.50
Water content: 9.4%

(2) 50 g of the product are dried at 60° C. in hot air (relative humidity: 20%) for 24 hours, whereby 45.3 g of monopotassium L-malate are obtained.
M.p.: 184°–185° C.
$[\alpha]_D^{22} - 6.1°$ (C=4, in water)
Water content: 0.12%

EXAMPLE 2

207.2 g (0.5 mole) of calcium hydrogen L-malate 6 hydrate ($C_8H_{10}O_{10} \cdot Ca \cdot 6H_2O$) are suspended in 300 ml of water, and 55 ml of 60% (by weight) sulfuric acid are added thereto. The precipitates of calcium sulfate are removed by filtration. The filtrate is passed through a column of about 100 ml of a cation exchange resin [manufactured by Rohm & Haas Co. under the trade name "Amberlite IR-120 ($H^+$ type)] and then a column of about 30 ml of an anion exchange resin [manufactured by Rohm & Haas Co. under the trade name "Amberlite IR-45 ($OH^-$ type)] to remove calcium sulfate completely therefrom. 79.2 g (1.4 moles) of potassium hydroxide (purity: 85%) are added gradually to the aqueous L-malic acid solution thus obtained. Insoluble materials are removed by filtration, and the filtrate (pH 4.4) is concentrated under reduced pressure to make the total weight thereof about 300 g. The concentrated filtrate is cooled to 10° C. and the mixture (i.e., the mixture of the concentrated filtrate and crystals precipitated) is stirred at the same temperature for 2 hours. After stirring the mixture had a pH of 5.6. The crystalline precipitates are collected by filtration, washed with an aqueous 80% methanol solution and dried overnight in air at 35° C. 133.6 g of monopotassium L-malate monohydrate are obtained as crystals. Yield: 70.2% The product loses its intramolecular water at 99° to 101° C. and decomposes at 183.5° to 185° C.

The amounts of L-malic acid, potassium and water contained in the product are shown in Table 1.

Table 1

|  | Calculated for $KC_4H_5O_5 \cdot H_2O$ (% by weight) | Found (% by weight) |
|---|---|---|
| L-malic acid | 70.6 | 70.4 |
| potassium | 20.5 | 20.3 |
| water | 9.4 | 9.6 |
| mole ratio of potassium to L-malic acid | 1 | 1 |

EXAMPLE 3

134.1 g (one mole) of L-malic acid and 71.8 g (0.52 mole) of potassium carbonate are dissolved in 130 ml of water at about 80° C. The solution (pH 4.2) is cooled to 20° C., and the mixture obtained (i.e., the mixture of the solution and crystals precipitated) is stirred at the same temperature for 4 hours. After stirring, the mixture had a pH of 5.2. The crystalline precipitates are collected from 20 ml of the mixture by filtration. The crystalline precipitates thus obtained are hereinafter referred to as "Crystals I."

On the other hand, the remaining mixture (about 250 ml) is adjusted to pH 5.5 with potassium hydroxide, and further stirred for 4 hours. After stirring, the mixture had a pH of 5.45. The crystalline precipitates are collected by filtration. The precipitates thus obtained are hereinafter referred to as "Crystals II". Yield: 121.5 g (63.9%)

Crystals I and II obtained above are washed with an aqueous 80% methanol solution and dried overnight in air at 35° C. The amounts of L-malic acid, potassium and water contained in Crystals I and II are respectively shown in Table 2, and the physicochemical properties of said crystals are shown in Table 3.

Table 2

|  | Calculated for $KC_4H_5O_5 \cdot H_2O$ (% by weight) | Found Crystals I (% by weight) | Found Crystals II (% by weight) |
|---|---|---|---|
| L-malic acid | 70.6 | 79.9 | 70.5 |
| potassium | 20.5 | 16.3 | 20.6 |
| water | 9.4 | 4.2 | 9.6 |
| mole ratio of potassium to L-malic acid | 1 | 0.7 | 1 |

Table 3

|  | Temperature at which the intramolecular water is removed. | M.p. | $[\alpha]_D^{22}$ (C = 4, $H_2O$) |
|---|---|---|---|
| Crystals I | — | 175°–177° C | −4.8° |
| Crystals II | 98°–100° C | 183.5°–185° C (decomp.) | −5.6° |

EXAMPLE 4

134.1 g (one mole) of L-malic acid and 120 g (1.20 moles) of potassium bicarbonate are dissolved at 60° C. in 200 ml of water. The solution (pH 4.4) is concentrated under reduced pressure to make the total volume thereof about 200 ml. The concentrated solution is cooled to 10° C., and the mixture obtained (i.e., the mixture of the concentrated solution and crystals precipitated) is stirred at the same temperature for 4 hours. After stirring, the mixture had a pH of 6.0. The crystalline precipitates are collected by filtration. 144.6 g of monopotassium L-malate monohydrate are obtained as crystals. Yield: 76%

EXAMPLE 5

(1) 46.2 g (0.334 mole) of potassium carbonate are dissolved in 500 ml of an aqueous L-malic acid solution[L-malic acid content: 75.9 g (0.566 mole)/500 ml]. The solution (pH 4.4) is concentrated at 60° C. under reduced pressure to make the total weight thereof about 170 g. The concentrated solution is cooled to 10° C., and the mixture obtained (i.e., the mixture of the concentrated solution and crystals precipitated) is stirred at the same temperature for 2 hours. After stirring, the mixture had a pH of 5.8. The crystalline precipitates are collected by filtration. 80.9 g of monopotassium potassium L-malate are obtained.

(2) The filtrate obtained in paragraph (1) is mixed with 500 ml of an aqueous L-malic acid solution[L-malic acid content: 75.9 g (0.566 mole)/500 ml], and 39 g (0.282 mole) of potassium carbonate are added thereto. The solution (pH 4.3) is concentrated to about 130 ml and cooled to 10° C. Then, the mixture thus obtained (i.e., the mixture of the concentrated solution and crystals precipitated) is adjusted to a pH 5.4 with potassium hydroxide, and stirred at the same temperature for 6 hours. After stirring, the mixture had the pH of 5.6. The crystalline precipitates are collected by filtration. 102.8 g of monopotassium L-malate monohydrate are obtained. Total amount: 183.7 g Yield: 85.4% (calculated on the basis of L-malic acid used)

EXAMPLE 6

(1) 34.2 g (0.61 mole) of potassium hydroxide are dissolved in 200 ml of an aqueous L-malic acid solution [L-malic acid content: 68.1 g (0.508 mole)/200 ml]. The solution (total weight: 234 g, pH 4.5) is concentrated under reduced pressure to make the total weight thereof 75 g. The concentrated solution is cooled to 10° C. Then, the mixture thus obtained (i.e., the mixture of the concentrated solution and crystals precipitated) is stirred at the same temperature for 3 hours. After stirring, the mixture had a pH of 5.5.

(2) The mixture obtained in paragraph (1) is adjusted to pH 4.85 with 15.2 g of an aqueous 34.07 w/w % L-malic acid solution, and stirred for one hour. The crystalline precipitates are collected by filtration, washed with an aqueous 80% methanol solution, and then dried overnight in air at 30° C. 76.2 g of monopotassium L-malate monohydrate are obtained as crystals. Yield: 73.3% The amounts of L-malic acid, potassium and water in the product are shown in Table 4.

Table 4

| | Calculated for KC$_4$H$_5$O$_5$·H$_2$O (% by weight) | Found (% by weight) |
|---|---|---|
| L-malic acid | 70.6 | 70.6 |
| potassium | 20.5 | 20.4 |
| water | 9.4 | 9.5 |
| mole ratio of potassium to L-malic acid | 1 | 1 |

EXAMPLE 7

(1) 26.8 g (0.20 mole) of L-malic acid and 8.0 g (0.20 mole) of sodium hydroxide are dissolved in 200 ml of water. The solution (pH 4.1) is concentrated under reduced pressure to make the total weight thereof 60 g. The concentrated solution is cooled to 10° C., and the mixture obtained (i.e., the mixture of the concentrated solution and crystals precipitated) is stirred at the same temperature for 4 hours. After stirring, the mixture had a pH of 4.1. The crystalline precipitates are collected by filtration, washed with an aqueous 80% methanol solution, and dried at 35° C. in air for 16 hours. 23.2 g of monosodium L-malate dihydrate are obtained as crystals. The amounts of L-malic acid, sodium and water contained in the product are shown in Table 5. The results set forth in this table indicate that the product obtained is the pure crystals of monosodium L-malate dihydrate.

Table 5

| | Calculated for NaC$_4$H$_5$O$_5$·H$_2$O (% by weight) | Found (% by weight) |
|---|---|---|
| L-malic acid | 69.3 | 69.4 |
| sodium | 12.0 | 12.0 |
| water | 18.7 | 18.6 |
| mole ratio of sodium to L-malic acid | 1 | 1 |

(2) 26.8 g (0.2 mole) of DL-malic acid and 13.8 g (0.1 mole) of potassium carbonate are dissolved in 200 ml of water. The solution (pH 4.1) is concentrated under reduced pressure to make the total weight thereof 60 g. The concentrated solution is cooled to 10° C., and the mixture obtained (i.e., the mixture of the concentrated solution and crystals precipitated) is stirred at the same temperature for 4 hours. After stirring, the mixture had a pH of 4.1. The crystalline precipitates are collected by filtration, washed with an aqueous 80% methanol solution, and dried at 35° C. for 16 hours. 26.4 g of monopotassium DL-malate monohydrate are obtained as crystals. The amounts of DL-malic acid, potassium and water contained in the product are shown in Table 6. The results of this table indicate that the product obtained is the pure crystals of monopotassium DL-malate monohydrate.

Table 6

| | Calculated for KC$_4$H$_5$O$_5$·H$_2$O (% by weight) | Found (% by weight) |
|---|---|---|
| DL-malic acid | 70.6 | 70.7 |
| potassium | 20.5 | 20.5 |
| water | 9.4 | 9.5 |
| mole ratio of potassium to DL-malic acid | 1 | 1 |

(3) 26.8 g (0.2 mole) of L-malic acid and 13.8 g (0.1 mole) of potassium carbonate are dissolved in 200 ml of water. The solution (pH 4.1) is concentrated under reduced pressure to make the total weight thereof 60 g. The concentrated solution is cooled to 10° C., and the mixture (i.e., the mixture of the concentrated solution and crystals precipitated) is stirred at the same temperature for 4 hours. After stirring, the mixture had a pH of 5.1. The crystalline precipitates are collected by filtration, washed with an aqueous 80% methanol solution, and dried at 35° C. in air for 16 hours. 23.4 g of monopotassium L-malate are obtained as crystals.

M.p. 174°–177° C.

$[\alpha]_D^{22} - 4.7°$ (C=4, in water)

The amounts of L-malic acid, potassium and water in the product are shown in Table 7. The results of this table indicate that the product obtained is not pure crystals of monopotassium L-malate monohydrate, but is composed of 0.7 mole of potassium and one mole of L-malic acid.

Table 7

| | Calculated for KC$_4$H$_5$O$_5$ (% by weight) | Found (% by weight) |
|---|---|---|
| L-malic acid | 77.3 | 82.7 |
| potassium | 22.7 | 17.3 |
| water | — | 1.9 |
| mole ratio of potassium to L-malic acid | 1 | 0.7 |

Concomitantly, the potassium L-malate obtained above gives an IR-spectrum quite different from monopotassium L-malate obtained in Example 1-(2).

Accordingly, the results of Tables 5 to 7 clearly show that, whereas monosodium L-malate and monopotassium DL-malate can be prepared in accordance with per se known methods, the monopotassium salt of L-malic acid is quite different from the corresponding sodium salt and monopotassium DL-malate in their properties and can not be prepared by conventional methods such as those employed for the preparation of monosodium L-malate and monopotassium DL-malate.

What we claim is:

1. A method of preparing monopotassium L-malate monohydrate which comprises cooling an aqueous solution of L-malic acid and potassium ion, said solution having a pH of 6.8 or less, to initiate crystallization of a potassium salt of L-malic acid, continuing said crystallization at a pH of 5.3 to 6.8, and recovering the resultant crystals of monopotassium L-malate monohydrate therefrom.

2. The method of claim 1, wherein said crystallization is continued at a pH of 5.3 to 6.5.

3. The method of claim 1, wherein said crystallization is continued until the mixture of crystals precipitated and said aqueous potassium L-malate solution substantially reaches liquid-solid equilibrium.

4. The method of claim 3, wherein said crystallization is continued at a pH of 5.3 to 6.5.

5. The method of claim 1, wherein said crystallization is continued by allowing the mixture of said aqueous potassium L-malate solution and crystals precipitated to stand at a pH of 5.3 to 6.8 until said mixture substantially reaches liquid-solid equilibrium.

6. The method of claim 5, wherein said mixture is allowed to stand at a pH of 5.3 to 6.5.

7. The method of claim 1, wherein the resultant crystals of monopotassium L-malate monohydrate are recovered at a pH of 4.8 to 6.8.

8. The method of claim 2, wherein the resultant crystals of monopotassium L-malate monohydrate are recovered at a pH of 4.8 to 6.8.

9. The method of claim 3, wherein the resultant crystals of monopotassium L-malate monohydrate are recovered at a pH of 4.8 to 6.8.

10. The method of claim 4, wherein the resultant crystals of monopotassium L-malate monohydrate are recovered at a pH of 4.8 to 6.8.

11. The method of claim 5, wherein the resultant crystals of monopotassium L-malate monohydrate are recovered at a pH of 4.8 to 6.8.

12. The method of claim 6, wherein the resultant crystals of monopotassium L-malate monohydrate are recovered at a pH of 4.8 to 6.8.

13. The method of claim 1, further including the step of drying the recovered crystals of monopotassium L-malate monohydrate to produce monopotassium L-malate anhydrate.

14. The method of claim 2, further including the step of drying the recovered crystals of monopotassium L-malate monohydrate to produce monopotassium L-malate anhydrate.

15. The method of claim 11, further including the step of drying the recovered crystals of monopotassium L-malate monohydrate to produce monopotassium L-malate anhydrate.

16. The method of claim 12, further including the step of drying the recovered crystals of monopotassium L-malate monohydrate to produce monopotassium L-malate anhydrate.

17. A method of preparing monopotassium L-malate monohydrate which comprises adding crystals, containing at least two components selected from the group consisting of L-malic acid, monopotassium L-malate and dipotassium L-malate, to water to thereby produce an aqueous mixture consisting essentially of said crystals and an aqueous potassium L-malate solution, adjusting the pH of the aqueous mixture to a range of 5.3 to 6.8, allowing the aqueous mixture to stand at said range until it substantially reaches liquid-solid equilibrium, and recovering the resultant crystals of monopotassium L-malate monohydrate therefrom.

18. The method of claim 17, wherein said range is 5.3 to 6.5.

19. The method of claim 17, wherein the resultant crystals of monopotassium L-malate monohydrate are recovered at a pH of 4.8 to 6.8.

20. The method of claim 17, wherein said range is 5.3 to 6.5, and the resultant crystals of monopotassium L-malate monohydrate are recovered at a pH of 4.8 to 6.8.

21. The method of claim 20, wherein crystals composed of L-malic acid and monopotassium L-malate are added to water to produce a mixture of said crystals added and an aqueous potassium L-malate solution.

22. The method of claim 17, further including the step of drying said resultant crystals of monopotassium L-malate monohydrate to produce monopotassium L-malate anhydrate.

23. The method of claim 21, further including the step of drying said resultant crystals of monopotassium L-malate monohydrate to produce monopotassium L-malate anhydrate.

* * * * *